United States Patent [19]

Cherkofsky et al.

[11] 4,318,917

[45] Mar. 9, 1982

[54] ANTIINFLAMMATORY 2,3-DIARYL-5-[2,2,2-TRIFLUORO-1-(TRIFLUOROMETHYL)ETHYL-1H-PYRROLES

[75] Inventors: Saul C. Cherkofsky; George A. Boswell, Jr., both of Wilmington, Del.

[73] Assignee: E. I. Du Pont de Nemours and Company, Wilmington, Del.

[21] Appl. No.: 261,197

[22] Filed: May 14, 1981

Related U.S. Application Data

[63] Continuation-in-part of Ser. No. 226,871, Jan. 21, 1981, which is a continuation-in-part of Ser. No. 170,872, Jul. 21, 1980, abandoned.

[51] Int. Cl.$^3$ .................... A61K 31/40; A61K 31/44; C07D 207/323; C07D 401/04
[52] U.S. Cl. .................... 424/274; 260/313.1; 260/326.5 R; 260/326.5 S; 260/326.5 SF; 260/326.5 L; 260/326.9; 424/263; 546/256; 546/281
[58] Field of Search .................... 424/263, 274; 260/326.5 J, 326.9, 313.1, 326.5 SF, 326.5 R, 326.5 L, 326.5 S; 546/256, 281

[56] References Cited

U.S. PATENT DOCUMENTS 3,564,016 2/1971 Schoen et al. .................... 260/313.1
3,709,906 1/1973 Yoshida et al. .................... 260/326.9

FOREIGN PATENT DOCUMENTS 7012853 3/1971 Netherlands .................... 260/326.9
7013607 3/1971 Netherlands .................... 260/326.9

OTHER PUBLICATIONS

Yoshida et al., Yakugaku Zasshi, vol. 92, pp. 1, 11, 305, 311 (1972).
Yoshida et al., Yakugaku Zasshi, vol. 93, p. 584 (1973).
Yoshida et al., Chem. Abstracts, vol. 84, Abstract No. 180032c (1976).

Primary Examiner—Alton D. Rollins

[57] ABSTRACT

Antiinflammatory 2,3-diaryl-5-[2,2,2-trifluoro-1-(trifluoromethyl)ethyl]-1H-pyrroles, such as 2,3-bis(4-fluorophenyl)-5-[2,2,2-trifluoro-1-(trifluoromethyl)ethyl]-1H-pyrrole, useful for treating arthritis and related diseases.

35 Claims, No Drawings

ANTIINFLAMMATORY 2,3-DIARYL-5-[2,2,2-TRIFLUORO-1-(TRI-FLUOROMETHYL)ETHYL-1H-PYRROLES

RELATED APPLICATION

This is a continuation-in-part of Ser. No. 226,871, filed Jan. 21, 1981, which is a continuation-in-part of Ser. No. 170,872, filed July 21, 1980, abandoned.

BACKGROUND OF THE INVENTION

This invention relates to antiinflammatory pyrroles.

J. Szmuszkovicz et al., *J. Med. Chem.*, 9 (4), 527 (1966) describe the synthesis and biological activity of an antiinflammatory agent of the formula:

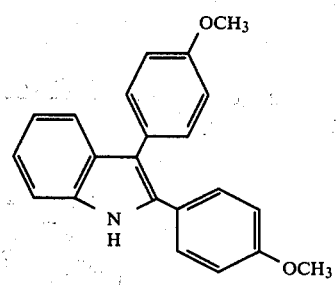

Yoshida et al. in U.S. Pat. No. 3,709,906 and other references including *Experientia*, 28, (8) 937 (1972) and *Yakugaku Zasshi*, 92, 1 (1972); 92, 11 (1972); 92, 305 (1972); 92, 311 (1972); and 93, 584 (1973) disclose 5-alkyl-2,3-diarylpyrroles, including 2,3-bis(4-methoxyphenyl)-5-methyl-1H-pyrrole

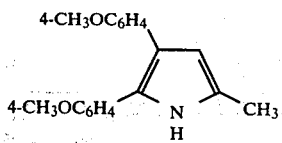

("bimetopyrol"), which are useful as antiinflammatory agents.

R. W. Guy and R. Alan Jones, *Aust. J. Chem.*, 19, 1871 (1966) describe the synthesis of 2,3-diphenyl-5-methyl-1H-pyrrole.

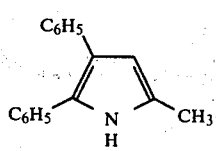

A. Laurent et al., *Tetrahedron Letters*, 18, 1587 (1979) describe the synthesis of 4,5-dimethyl-2,3-diphenyl-1H-pyrrole.

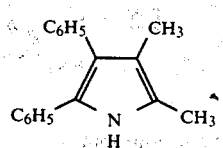

There is a continuing need for safe and effective antiinflammatory agents. Inflammation is a disease process characterized by redness, fever, swelling and pain. Arthritis in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side effects. Many produce gastric irritation and other effects, such as change in blood cells and central nervous system. Adrenocortical steroids produce gastric irritation and suppression of normal adrenal function.

SUMMARY OF THE INVENTION

This invention relates to compounds of formula I, pharmaceutical compositions containing them and methods of use of these compounds to treat arthritis and relieve inflammation in mammals.

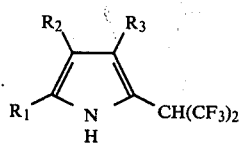

where $R_1$ and $R_2$ independently = 3-pyridyl or

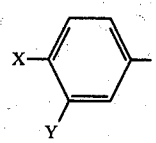

where $X$=H, F, Cl, Br, $C_1$-$C_2$ alkyl, $C_1$-$C_2$ alkoxy, di($C_1$-$C_2$ alkyl)amino or $CH_3S(O)_n$ where n=0, 1 or 2;

$Y$=H, F or Cl; provided when $Y$=F or Cl, $X$ must=F or Cl;

$R_3$=H or $C_1$-$C_3$ alkyl;

or its pharmaceutically suitable acid addition salt where at least one of $R_1$ or $R_2$=3-pyridyl or $X$=di($C_1$-$C_2$ alkyl)amino.

Also, this invention relates to novel intermediates of formula II useful for preparation of the antiinflammatory formula I compounds

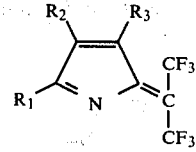

where $R_1$, $R_2$ and $R_3$ are as defined in formula I.

In addition to being useful as intermediates to antiinflammatory compounds of formula I, some of the compounds within the scope of formula II are themselves useful in treatment of inflammation as demonstrated by test results of representative compounds.

Preferred Compounds

Preferred compounds of formula I are those where independently:

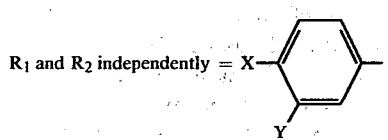

where
X=H, F, Cl, Br or CH$_3$S; and
Y=H; or
(2) R$_3$=H.

More preferred compounds of Formula I are those where:
R$_1$ and R$_2$ independently=

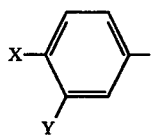

where
X=H, F, Cl, Br or CH$_3$S;
Y=H; and
R$_3$=H.

Examples of compounds preferred are where:
(1) R$_1$ and R$_2$=C$_6$H$_5$—; R$_3$=H; and
(2) R$_1$ and R$_2$=4-FC$_6$H$_4$—; R$_3$=H; and
(3) R$_1$=4-CH$_3$SC$_6$H$_4$—; R$_2$=4-FC$_6$H$_4$—; R$_3$=H; and
(4) R$_1$=4-BrC$_6$H$_4$—; R$_2$=4-FC$_6$H$_4$—; R$_3$=H; and
(5) R$_1$ and R$_2$=4-ClC$_6$H$_4$—; R$_3$=H.

Preferred Compounds

Compounds of Formula II that are preferred as intermediates to antiinflammatory compounds of Formula I and/or as antiinflammatory compounds themselves are those where, independently,

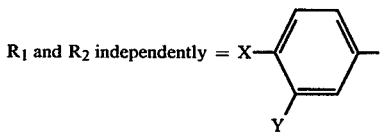

where
X=H, F, Cl, Br or CH$_3$S;
Y=H; or
(2) R$_3$=H.

More preferred compounds of formula II are those where R$_1$ and R$_2$ independently

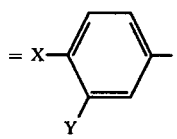

where X=H, F, Cl, Br or CH$_3$S; Y=H; and R$_3$=H.

Compounds of Formula II which are preferred are:
(1) 4,5-bis(4-fluorophenyl)-2-[2,2,2-trifluoro-1-(trifluoromethyl)ethylidene]-2H-pyrrole; and
(2) 5-(4-bromophenyl)-4-(4-fluorophenyl)-2-[2,2,2-trifluoro-1-(trifluoromethyl)ethylidene]-2H-pyrrole; and (3) 4-(4-fluorophenyl)-5-(4-methylthiophenyl-2-[2,2,2-trifluoro-1-(trifluoromethyl)ethylidene]-2H-pyrrole.

Synthesis

The compounds of this invention can be prepared from 2,3-diarylpyrroles, methods for the preparation of which are described in European Pat. 5,156 (U.S. patent application Ser. No. 10,259, filed Feb. 8, 1979), abandoned.

Reaction of 2,3-diarylpyrroles with the cyclic dimer of hexafluorothioacetone [2,2,4,4-tetrakis(trifluoromethyl)-1,3-dithietane] in the presence of phosphines, such as triphenyl phosphine, gives the products containing a hexafluoroisopropyl group in the 5-position of the pyrrole. This reaction

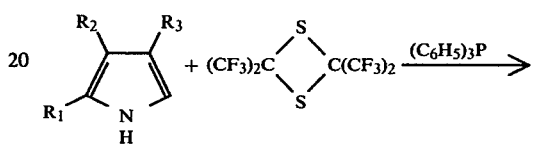

is run in solution in an inert solvent, such as toluene or the like, usually at the boiling point of the solvent.

Alternatively, the hexafluoroisopropyl group can be introduced by a three-step process involving (1) introduction of a hexafluoroisopropanol group into a diaryl pyrrole,

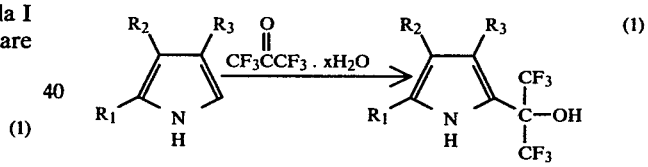

(2) dehydration of the alcohol to an azafulvene and

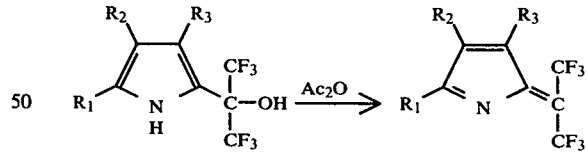

(3) reduction of the azafulvene to the desired

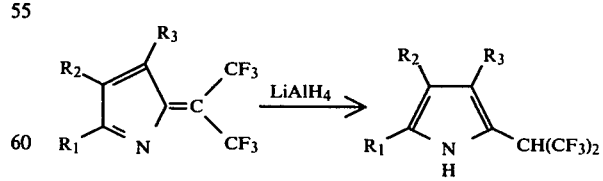

hexafluoroisopropyl compound.

Introduction of the hexafluoroisopropanol group [reaction (1)] is accomplished by reaction of the 2,3-diarylpyrrole with hexafluoroacetone or its various hydrates. This reaction may be conducted in a sealed pressure reactor at a temperature from ambient to 200°

C. It can also be conducted in a refluxing solvent, such as toluene, in a flask with hexafluoroacetone or its various hydrates. Acidic catalysts, such as $AlCl_3$, $BF_3$, p-toluenesulfonic acid or trifluoroacetic acid, can be used but are not required. Reaction times are usually 4–24 hours. The use of hexafluoroacetone trihydrate in refluxing toluene without catalyst is preferred.

The dehydration to the azafulvenes [reaction (2)] can be run with standard dehydrating agents. The preferred conditions involve heating the alcohol in excess acetic anhydride (as solvent) at reflux for several hours.

The reduction of the azafulvenes [reaction (3)] can be accomplished either by catalytic-hydrogenation or by metal hydride reduction. The preferred conditions involve lithium aluminum hydride in ether at room temperature.

The preparation of these compounds is further illustrated by the following examples. In the following examples, all temperatures are in degrees Centigrade.

EXAMPLE 1

2,3-Diphenyl-5-[2,2,2-trifluoro-1-(trifluoromethyl)-ethyl]-1H-pyrrole

To a solution of 2.2 g (0.01 mole) of 2,3-diphenyl-1H-pyrrole in 50 ml ether at $-78°$ under nitrogen were added 3.64 g (0.01 mole) of 2,2,4,4-tetrakis(trifluoromethyl)-1,3-dithietane and 0.26 g (0.001 mole) of triphenylphosphine. The reaction mixture was stirred at $-78°$ for one hour, then allowed to warm to room temperature. The tlc indicated very little reaction, so the ether solvent was removed by distillation, gradually adding toluene to replace it. The toluene solution was then heated at reflux for 1.5 hours. Then additional amounts of the dithietane (3.64 g) and triphenylphosphine (0.26 g) in 1 ml toluene were added and the mixture was heated at reflux overnight. The mixture was concentrated on a rotary evaporator and the residue was purified first by column chromatography on 400 g silica gel (eluting with 60/40 hexane/toluene) then by preparative HPLC to give, after recrystallization from hexane, 0.5 g (14%) of 2,3-diphenyl-5-[2,2,2-trifluoro-1-(trifluoromethyl)ethyl]-1H-pyrrole, m.p. 112°–114°. The ir and nmr (proton and fluorine) were consistent with the assigned structure.

Mass Spectrum Calcd. 369.0899; Found: 369.0925

Anal. Calcd. for $C_{19}H_{13}F_6N$: C, 61.79; H, 3.54; N, 3.79. Found: C, 61.99, 62.14; H, 3.34, 3.64; N, 3.87, 4.03.

EXAMPLE 2

2,3-Bis(4-fluorophenyl)-5-[2,2,2-trifluoro-1-(trifluoromethyl)ethyl]-1H-pyrrole

Method A

To a solution of 2.6 g (0.01 mole) of 2,3-bis(4-fluorophenyl)-1H-pyrrole in 50 ml toluene were added 3.64 g (0.01 mole) of 2,2,4,4-tetrakis(trifluoromethyl)-1,3-dithietane and 2.62 g (0.01 mole) of triphenylphosphine. The reaction mixture was heated at reflux for 6 hours, then stirred at room temperature overnight. Analysis by tlc indicated that some starting material remained, so the mixture was heated at reflux another 8 hours, then stirred at room temperature overnight again. The mixture was concentrated by rotary evaporation and the residue was purified by column chromatography on 400 g silica gel (eluting with 50/50 hexane/toluene) followed by preparative HPLC to give, after recrystallization from hexane, 0.3 g (7%) of 2,3-bis-(4-fluorophenyl)-5-[2,2,2-trifluoro-1-(trifluoromethyl)ethyl]-1H-pyrrole, m.p. 126°–127.5°. The ir and nmr (proton and fluorine) were consistent with the assigned structure.

Mass Spectrum Calcd. 405.0764; Found: 405.0738.

Anal. Calcd. for $C_{19}H_{11}F_8N$: C, 56.31; H, 2.74 N, 3.46. Found: C, 56.44; H, 2.86; N, 3.43.

Method B a.

4,5-Bis(4-fluorophenyl)-α,α-di(trifluoromethyl)-1H-pyrrole-2-methanol

A mixture of 20.4 g (0.08 mole) of 2,3-bis(4-fluorophenyl)-1H-pyrrole and 19.8 g (0.09 mole) of hexafluoroacetone trihydrate in 300 ml toluene was heated at reflux for 6 hours. Analysis by tlc indicated a small amount of starting material remained so another 1.0 g of hexafluoroacetone trihydrate was added and the mixture was refluxed another 0.5 hour. After stirring at room temperature overnight, the mixture was concentrated by rotary evaporation. The residue was purified by chromatography on 2 pounds of silica gel, eluting with toluene. The chromatographed product was decolorized with charcoal, then recrystallized from hexane to give 21.5 g (63%) of product, m.p. 112°–113°.

Anal. Calcd. for $C_{19}H_{11}F_8NO$: C, 54.17; H, 2.63; N, 3.32. Found: C, 54.07; H, 2.97, N, 3.45.

b.

4,5-Bis(4-fluorophenyl)-2-[2,2,2-trifluoro-1-(trifluoromethyl)ethylidene]-2H-pyrrole (Example 17)

A mixture of 4.2 g (0.01 mole) of 4,5-bis(4-fluorophenyl)-α,α-di(trifluoromethyl)-1H-pyrrole-2-methanol and 100 ml acetic anhydride was heated at reflux under nitrogen for 3 hours. The mixture was cooled and concentrated under vacuum. The residue was purified by column chromatography on 400 g of silica gel. Eluted with 50/50 hexane/toluene was 4,5-bis(4-fluorophenyl)-2[2,2,2-trifluoro-1-(trifluoromethyl)-ethylidene]-2H-pyrrole, obtained after recrystallization from hexane as a yellow-orange solid, 1.8 g (45%), m.p. 145°–146°. The ir and nmr (proton and fluorine) spectra were consistent with the assigned structure.

Mass spectrum Calcd. $C_{19}H_9F_8N$: 403.0607. Found: 403.0590.

Anal. Calcd. for $C_{19}H_9F_8N$: C, 56.59; H, 2.25; N, 3.47. Found: C, 56.71; H, 2.35; N, 3.48.

c.

2,3-Bis(4-fluorophenyl)-5-[2,2,2-trifluoro-1-(trifluoromethyl)ethyl]-1H-pyrrole (Example 2)

To a mixture of 0.57 g (0.015 mole) of lithium aluminum hydride in 200 ml ether under nitrogen was added dropwise a solution of 4.03 g (0.01 mole) of 4,5-bis(4-fluorophenyl)-2-[2,2,2-trifluoro-1-(trifluoromethyl)ethylidene]-2H-pyrrole in 50 ml ether. The mixture was stirred at room temperature for 2 hours, then water was added cautiously dropwise. Finally approximately 50 ml of 1 N HCl was added and the ether layer was separated. The aqueous layer was further extracted with ether. The combined ether layers were dried and concentrated under vacuum. The residue was purified by column chromatography on 450 g slica gel, eluting with 75/25 hexane/toluene to give, after recrystallization from hexane, 1.6 g (40%) of product, m.p. 123°–124°, identical by ir and tlc to product obtained by Method A.

Other 2,3-diaryl-5-[2,2,2-trifluoro-1-(trifuoromethyl)ethyl]-1H-pyrroles that can be prepared by the procedures described are illustrated in Table 1.

Other 4,5-diaryl-2-[2,2,2-trifluoro-1-(trifluoromethyl-)ethylidene]-2H-pyrroles that can be preferred by the procedures described are illustrated in Table 2.

TABLE 1

$$R_1-C(=N(H))-C(R_2)=C(R_3)-CH(CF_3)_2$$

| Example | R₁ | R₂ | R₃ | m.p. | Yield |
|---|---|---|---|---|---|
| 3 | 4-ClC₆H₄ | 4-ClC₆H₄ | H | 125–130° | 28% |
| 4 | 4-BrC₆H₄ | 4-FC₆H₄ | H | 117–1117.5° | 21% |
| 4 | 3-pyridyl | 4-FC₆H₄ | H | 200° (subl.) | 3% |
| 6 | 4-CH₃SC₆H₄ | 4-FC₆H₄ | H | 93–93.5° | 13% |
| 7 | 4-CH₃OC₆H₄ | 4-CH₃OC₆H₄ | H | | |
| 8 | 3,4-Cl₂C₆H₃ | C₆H₅ | H | | |
| 9 | 4-CH₃C₆H₄ | 4-CH₃C₆H₄ | H | | |
| 10 | 4-(CH₃)₂NC₆H₄ | 4-FC₆H₄ | H | | |
| 11 | 4-CH₃SO₂C₆H₄ | 4-FC₆H₄ | H | | |
| 12 | 4-FC₆H₄ | 4-FC₆H₄ | CH₃ | | |
| 13 | 4-C₂H₅C₆H₄ | 4-C₂H₅C₆H₄ | H | | |
| 14 | 4-C₂H₅OC₆H₄ | 4-C₂H₅OC₆H₄ | H | | |
| 15 | 4(C₂H₅)₂NC₆H₄ | 4-FC₆H₄ | H | | |
| 16 | 4-FC₆H₄ | 4-FC₆H₄ | n-C₃H₇ | | |

TABLE 2

$$R_1-C(=N)-C(R_2)=C(R_3)-C(CF_3)_2$$

| Example | R₁ | R₂ | R₃ | m.p. | Yield |
|---|---|---|---|---|---|
| 17 | 4-FC₆H₄ | 4-FC₆H₄ | H | 145–146° | 45% |
| 18 | 4-BrC₆H₄ | 4-FC₆H₄ | H | 150–151° | 43% |
| 19 | 4-CH₃SC₆H₄ | 4-FC₆H₄ | H | 106–107° | 32% |
| 20 | 4-ClC₆H₄ | 4-ClC₆H₄ | H | 121–124° | 15% |
| 21 | 4-CH₃OC₆H₄ | 4-CH₃OC₆H₄ | H | | |
| 22 | 3,4-Cl₂C₆H₃ | C₆H₅ | H | | |
| 23 | 3-pyridyl | 4-FC₆H₄ | H | | |
| 24 | 4-CH₃C₆H₄ | 4-CH₃C₆H₄ | H | | |
| 25 | 4-(CH₃)₂NC₆H₄ | 4-FC₆H₄ | H | | |
| 26 | 4-CH₃SO₂C₆H₄ | 4-FC₆H₄ | H | | |
| 27 | 4-FC₆H₄ | 4-FC₆H₄ | CH₃ | | |
| 28 | 4-ClC₆H₄ | 4-FC₆H₄ | H | | |
| 29 | 4-FC₆H₄ | 4-FC₆H₄ | C₃H₇— | | |
| 30 | 4-C₂H₅C₆H₄ | 4-C₂H₅C₆H₄ | H | | |
| 31 | 4-C₂H₅OC₆H₄ | 4-C₂H₅OC₆H₄ | H | | |
| 32 | 4-(C₂H₅)₂NC₆H₄ | 4-FC₆H₄ | H | | |

Dosage Forms

The anti-arthritic agents of formula I can be administered to treat arthritis by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.05 to 40 milligrams per kilogram of body weight. Ordinarily 0.1 to 20, and preferably 0.2 to 10 milligrams per kilogram per day given in divided doses 2 to 4 times a day or in sustained release form is effective to obtain desired results.

Dosage forms (compositions) suitable for internal administration contain from about 5 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tables. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of formula I can be illustrated as follows:

Capsules

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized by commonly used techniques.

Suspension

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Pharmaceutical Utility

A procedure for detecting and comparing the antiinflammatory activity of compounds in this series and standard drugs for which there is a good correlation with human efficacy is the adjuvant-induced arthritis test in rats.

The test procedure employed for determining antiinflammatory activity is described below.

Established Adjuvant-Induced Arthritis in Rats

Charles River Lewis male rats (130–150 grams) are injected subcutaneously in plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum Acacia, U.S.P. 5%, Methylparaben 0.5%) (10 ml/kg) by gavage on that day and on the 6 following days. One day after the last dose the paw volumes (uninjected, left hind paw) are measured using a Ugo Basile Volume Differential Meter Model 7101.

$$\frac{\frac{\text{Arthritic Control}}{\text{Mean Paw Volume (ml)}} - \frac{\text{Treatment Group}}{\text{Mean Paw Volume (ml)}}}{\frac{\text{Arthritic Control}}{\text{Mean Paw Volume (ml)}} - \frac{\text{Non-Arthritic Control}}{\text{Mean Paw Volume (ml)}}} \times 100 =$$

% Decrease from Control Mean Paw Volume.

Dose-response regression lines of the % decrease are plotted on semi-log paper by visual fit and the ED50% decrease from control paw volume is determined by inspection.

TABLE 3

Adjuvant Arthritis Activity

[Structure: pyrrole with $R_1$, $R_2$, $R_3$, N-$R_1$, $CH(CF_3)_2$]

| Example | $R_1$ | $R_2$ | $R_3$ | Adjuvant Arthritis $ED_{50}$ (mg/kg) |
|---------|-------|-------|-------|--------------------------------------|
| 1 | $C_6H_5$ | $C_6H_5$ | H | 11 |
| 2 | $4\text{-}FC_6H_4$ | $4\text{-}FC_6H_4$ | H | 4 |
| 3 | $4\text{-}ClC_6H_4$ | $4\text{-}ClC_6H_4$ | H | 15 |
| 4 | $4\text{-}BrC_6H_4$ | $4\text{-}FC_6H_4$ | H | 3.9 |
| 5 | 3-pyridyl | $4\text{-}FC_6H_4$ | H | 0% at 5 mg/kg)[1,2] |
| 6 | $4\text{-}CH_3SC_6H_4$ | $4\text{-}FC_6H_4$ | H | 2.5 |

TABLE 4

Adjuvant Arthritis Activity

[Structure with $R_1$, $R_2$, $R_3$, N, C(CF_3)_2]

| Example | $R_1$ | $R_2$ | $R_3$ | Adjuvant Arthritis $ED_{50}$ (mg/kg) |
|---------|-------|-------|-------|--------------------------------------|
| 17 | $4\text{-}FC_6H_4$ | $4\text{-}FC_6H_4$ | H | 33 |
| 18 | $4\text{-}BrC_6H_4$ | $4\text{-}FC_6H_4$ | H | (16% at 25 mg/kg)[1] |

[1]Values in parentheses indicate the percent reduction in paw volume at the indicated dose.
[2]Although inactive at the dose tested, this compound would be expected to be active when tested at higher dose levels.

What is claimed is:

1. A compound of the formula

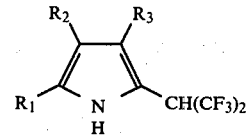

where
$R_1$ and $R_2$ independently = 3-pyridyl or

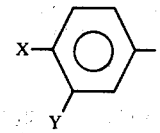

where
X=H, F, Cl, Br, $C_1$-$C_2$ alkyl, $C_1$-$C_2$ alkoxy, di($C_1$-$C_2$-alkyl)amino or $CH_3S(O)_n$ where n=0, 1 or 2;
Y=H, F or Cl; provided when Y=F or Cl, X must=F or Cl;
$R_3$=H or $C_1$-$C_3$ alkyl;
or its pharmaceutically suitable acid addition salt where at least one of $R_1$ or $R_2$=3-pyridyl or X=di($C_1$-$C_2$ alkyl)amino.

2. A compound of claim 1 wherein $R_1$ and $R_2$ independently

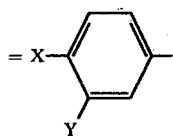

where X=H, F, Cl, Br or CH₃S; and Y=H.

3. A compound of claim 1 wherein R₃=H.
4. A compound of claim 1 wherein R₁ and R₂ independently

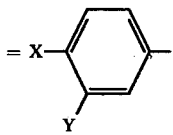

where X=H, F, Cl, Br or CH₃S; Y=H; and R₃=H.
5. The compound of claim 1 wherein R₁ and R₂

and R₃=H.
6. The compound of claim 1 wherein R₁ and R₂

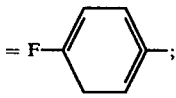

and R₃=H.
7. The compound of claim 1 wherein

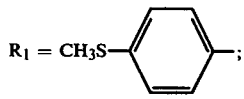

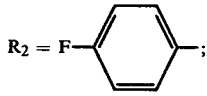

and R₃=H.
8. The compound of claim 1 wherein

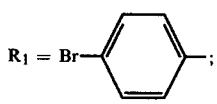

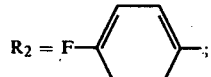

and R₃=H.
9. The compound of claim 1 wherein R₁ and R₂

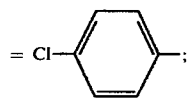

and R₃=H.

10. A pharmaceutical composition consisting essentially of a suitable pharmaceutical carrier and an effective antiinflammatory amount of a compound of claim 1.

11. A pharmaceutical composition consisting essentially of a suitable pharmaceutical carrier and an effective antiinflammatory amount of a compound of claim 2.

12. A pharmaceutical composition consisting essentially of a suitable pharmaceutical carrier and an effective antiflammatory amount of a compound of claim 3.

13. A pharmaceutical composition consisting essentially of a suitable pharmaceutical carrier and an effective antiinflammatory amount of a compound of claim 4.

14. A pharmaceutical composition consisting essentially of a suitable pharmaceutical carrier and an effective antiinflammatory amount of the compound of claim 5.

15. A pharmaceutical composition consisting essentially of a suitable pharmaceutical carrier and an effective antiinflammatory amount of the compound of claim 6.

16. A pharmaceutical composition consisting essentially of a suitable pharmaceutical carrier and an effective antiinflammatory amount of the compound of claim 7.

17. A pharmaceutical composition consisting essentially of a suitable pharmaceutical carrier and an effective antiinflammatory amount of the compound of claim 8.

18. A pharmaceutical composition consisting essentially of a suitable pharmaceutical carrier and an effective antiinflammatory amount of the compound of claim 9.

19. A method of treating inflammation in a mammal which comprises administering to the mammal an antiinflammatory amount of a compound of claim 1.

20. A method of treating inflammation in a mammal which comprises administering to the mammal an antiinflammatory amount of a compound of claim 2.

21. A method of treating inflammation in a mammal which comprises administering to the mammal an antiinflammatory amount of a compound of claim 3.

22. A method of treating inflammation in a mammal which comprises administering to the mammal an antiinflammatory amount of a compound of claim 4.

23. A method of treating inflammation in a mammal which comprises administering to the mammal an antiinflammatory amount of the compound of claim 5.

24. A method of treating inflammation in a mammal which comprises administering to the mammal an antiinflammatory amount of the compound of claim 6.

25. A method of treating inflammation in a mammal which comprises administering to the mammal an antiinflammatory amount of the compound of claim 7.

26. A method of treating inflammation in a mammal which comprises administering to the mammal antiinflammatory amount of the compound of claim 8.

27. A method of treating inflammation in a mammal which comprises administering to the mammal an anti-inflammatory amount of the compound of claim 9.

28. A method of forming a compound of claim 1 which comprises:

(A) contacting

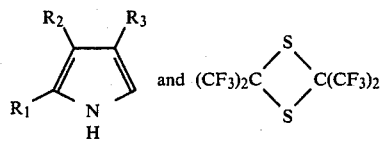

to produce a compound of claim 1; or (B) reducing

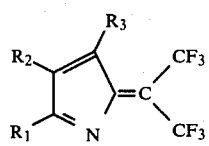

to produce a compound of claim 1.

29. A compound of the formula

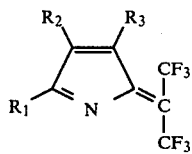

where $R_1$ and $R_2$ independently = 3-pyridyl or

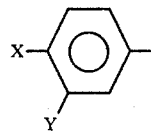

where
$X = H$, F, Cl, Br, $C_1-C_2$ alkyl, $C_1-C_2$ alkoxy, di($C_1-C_2$-alkyl)amino or $CH_3S(O)_n$ where $n=0$, 1 or 2;
$Y = H$, F or Cl; provided when $Y = F$ or Cl, X must = F or Cl;
$R_3 = H$ or $C_1-C_3$ alkyl.

30. A compound of claim 29 wherein $R_1$ and $R_2$ independently

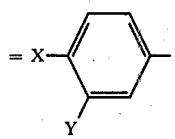

where $X = H$, F, Cl, Br or $CH_3S$; and $Y = H$.

31. A compound of claim 29 wherein $R_3 = H$.

32. A compound of claim 29 wherein $R_1$ and $R_2$ independently

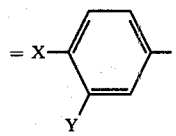

where $X = H$, F, Cl, Br or $CH_3S$; $Y = H$; and $R_3 = H$.

33. The compound of claim 29 which is 4,5-bis(4-fluorophenyl)-2-[2,2,2-trifluoro-1-(trifluoromethyl)ethylidene]-2H-pyrrole.

34. The compound of claim 29 which is 5-(4-bromophenyl)-4-(4-fluorophenyl)-2-[2,2,2-trifluoro-1-(trifluoromethyl)ethylidene]-2H-pyrrole.

35. The compound of claim 29 which is 4-(4-fluorophenyl)-5-(4-methylthiophenyl)-2-[2,2,2-trifluoro-1-(trifluoromethyl)ethylidene]-2H-pyrrole.

* * * * *